US00PP22957P2

(12) United States Plant Patent
Bergman

(10) Patent No.: US PP22,957 P2
(45) Date of Patent: Aug. 14, 2012

(54) *CHRYSANTHEMUM* PLANT NAMED 'CIDZ0004'

(50) Latin Name: *Chrysanthemum×morifolium*
Varietal Denomination: CIDZ0004

(75) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 13/136,485

(22) Filed: Aug. 2, 2011

(51) Int. Cl.
*A01H 5/00* (2006.01)

(52) U.S. Cl. ..... Plt./294

(58) Field of Classification Search ..... Plt./288, Plt./294
See application file for complete search history.

*Primary Examiner* — June Hwu
*Assistant Examiner* — Louanne Krawczewicz Myers
(74) *Attorney, Agent, or Firm* — Joshua L. Price

(57) ABSTRACT

A new *Chrysanthemum* plant named 'CIDZ0004' particularly distinguished by the daisy-type, clear white ray floret color, medium green foliage, vigorous growth habit, excellent flowering uniformity and is a fast finish crop at about seven weeks response.

1 Drawing Sheet

Latin name of the genus and species of the plant claimed: *Chrysanthemum×morifolium.*

Varietal denomination: 'CIDZ0004'.

BACKGROUND OF THE NEW PLANT

The present invention comprises a new *Chrysanthemum*, botanically known as *Chrysanthemum×morifolium*, and hereinafter referred to by the variety name 'CIDZ0004'.

'CIDZ0004' is a product of a planned breeding program. The new cultivar has daisy-type, clear white ray floret color, medium green foliage, vigorous growth habit, excellent flowering uniformity and is a fast finish crop at about seven weeks response.

'CIDZ0004' originated from a hybridization made in February 2006 in a controlled breeding environment in Salinas, Calif., USA. The female parent was the proprietary plant designated 'YB-A9154', unpatented, with yellow ray floret color and a smaller inflorescence size.

The male parent of 'CIDZ0004' was an unpatented, proprietary plant identified as 'YB-A9028' with white ray floret color, and produces pollen. The resultant seed was sown in July 2006 in Fort Myers, Fla., USA.

'CIDZ0004' was selected as one flowering plant within the progeny of the stated cross in November 2006 in a controlled environment in Fort Myers, Fla., USA.

The first act of asexual reproduction of 'CIDZ0004' was accomplished when vegetative cuttings were propagated from the initial selection in February 2007 in a controlled environment in Fort Myers, Fla., USA.

BRIEF SUMMARY OF INVENTION

Horticultural examination of plants grown from cuttings of the plant initiated in February 2007, and continuing thereafter, has demonstrated that the combination of characteristics as herein disclosed for 'CIDZ0004' are firmly fixed and are retained through successive generations of asexual reproduction.

'CIDZ0004' has not been observed under all possible environmental conditions. The phenotype may vary significantly with variations in environment such as temperature, light intensity and day length.

A Plant Breeder's Right for this cultivar was applied for in Canada on Aug. 17, 2010 (10-7062). 'CIDZ0004' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIDZ0004' with colors being as true as possible with an illustration of this type. The photographic drawing shows 4 flowering potted plants of the new variety, and a close-up of the inflorescences.

DETAILED BOTANICAL DESCRIPTION

The plant descriptions, measurements and aforementioned photographs were taken in Gilroy, Calif. in mid May 2011 under natural light. These plants were propagated and grown in Nipomo, Calif. and shipped to Gilroy, Calif. for the data collection and photographs. These plants were approximately 11 weeks of age; grown as four plants together in a six inch pot under greenhouse trial conditions.

Color references are made to The Royal Horticultural Society Colour Chart (R.H.S.) 2001.

TABLE 1

DIFFERENCES BETWEEN THE NEW VARIETY 'CIDZ0004' AND A MOST SIMILAR VARIETY

| | 'CIDZ0004' | 'Yojuneau' (U.S. Plant Pat. No. 20,560) |
|---|---|---|
| Flowering response: | 1 week faster | 1 week slower |
| Plant growth: | More vigorous | Less vigorous/less full |
| Inflorescence size: | Little larger | Little smaller |
| Ray floret length: | Little longer | Little shorter |

Plant:

*Form, growth and habit*.—Herbaceous pot-type, stems upright and outwardly spreading, freely branching, strong and moderately vigorous growth habit.

*Plant height*.—20-22.0 cm.

*Plant height* (*inflorescence included*).—29-33.0 cm.

*Plant width*.—18-24.0 cm.

Roots:

*Number of days to initiate roots*.—About 4 days at about 22 degrees C.

*Number of days to produce a rooted cutting*.—About 10 days at 22 degrees C.

*Type*.—Fine, fibrous, free branching.

*Color*.—RHS N155B but whiter.

Foliage:

*Arrangement*.—Alternate, simple.

*Immature, leaf color, upper surface*.—RHS 137A but darker.

*Lower surface*.—RHS 137B.

*Mature, leaf color, upper surface*.—RHS 137A but darker.

*Lower surface*.—RHS 137B.

*Length*.—5.8-6.5 cm.

*Width*.—4.4-4.6 cm.

*Shape*.—Ovate.

*Base shape*.—Attenuate.

*Apex shape*.—Mucronulate.

*Margin*.—Palmately lobed; irregularly serrate.

*Texture, upper surface*.—Bifid T-shaped hairs.

*Lower surface*.—Bifid T-shaped hairs.

*Color of veins, upper surface*.—RHS 144A.

*Color of veins, lower surface*.—RHS 144A.

*Petiole color*.—RHS 144A.

*Venation pattern*.—Palmate.

*Length*.—1.5-1.7 cm.

*Diameter*.—0.3 cm.

*Texture*.—Bifid T-shaped hairs.

Stem:

*Quantity of main branches per plant*.—3-4.

*Color of stem*.—RHS 143A.

*Length of stem*.—17-20.0 cm.

*Diameter*.—0.4-0.5 cm.

*Length of internodes*.—0.5-1.5 cm.

*Texture*.—Bifid T-shaped hairs.

*Color of peduncle*.—RHS 143A.

*Length of peduncle*.—6.9-7.7 cm.

*Peduncle diameter*.—0.2 cm.

*Texture*.—Bifid T-shaped hairs.

Inflorescence:

*Type*.—Compositae type, daisy-type inflorescences borne terminally above foliage, ray florets arranged acropetally on a capitulum.

*Quantity of short days to flowering* (*response time*).—About 7 weeks.

*Natural season flowering*.—Not determined on this variety.

*Quantity of inflorescences per plant*.—20-30.

*Lastingness of individual blooms on the plant*.—About 4 weeks.

*Fragrance*.—Slightly spicy.

Bud (just when opening/showing color):

*Color*.—RHS N155D but whiter.

*Length*.—1.0-1.5 cm.

*Width*.—0.7-1.0 cm.

*Shape*.—Oblate.

Immature inflorescence:

*Diameter*.—5.3-5.6 cm.

*Color of ray florets, upper surface*.—RHS N155D but whiter.

*Lower surface*.—RHS N155D but whiter.

Mature inflorescence:

*Diameter*.—7.-8.0 cm.

*Depth*.—1.5-2.0 cm.

*Total diameter of disc*.—1.5-1.6 cm.

*Receptacle color*.—RHS 144B.

*Receptacle height*.—0.8-1.1 cm.

*Receptacle diameter*.—0.9-1.0 cm.

Ray florets:

*Average quantity of florets*.—22-25 in 1-3 whorls.

*Color of florets, upper surface*.—RHS N155D but whiter.

*Lower surface*.—RHS N155D but whiter.

*Length*.—3.4-3.6 cm.

*Width*.—1.0-1.2 cm.

*Shape*.—Elliptical.

*Apex shape*.—Obtuse to some praemorse.

*Base shape*.—Cuneate.

*Margin*.—Entire.

*Texture, upper surface*.—Papillose.

*Lower surface*.—Papillose.

Disc florets:

*Average quantity of florets*.—Approximately 200.

*Color of florets*.—RHS 1C but greener, with RHS 5A apex.

*Length*.—0.5 cm.

*Width*.—0.1 cm.

*Shape*.—Tubular, elongated.

*Apex shape*.—Acute, 5 pointed.

*Texture, inner surface*.—Glabrous.

*Texture, outer surface*.—Glabrous.

Phyllaries:

*Quantity*.—25-30.

*Color, lower surface*.—RHS 137A.

*Inner surface*.—RHS 137B.

*Length*.—0.7-0.9 cm.

*Width*.—0.2-0.4 cm.

*Shape*.—Lanceolate.

*Apex shape*.—Acute.

*Base*.—Fused.

*Margins*.—Entire; papery with RHS 177B margins.

*Texture, upper surface*.—Glabrous.

*Lower surface*.—Bifid T-shaped hairs.

Reproductive organs:

*Pistil*.—1.

*Found on both florets*.—Yes.

*Length*.—0.5 cm.

*Style color*.—RHS 1C but greener.

*Style length*.—0.4 cm.

*Stigma color*.—RHS 7A.

*Stigma shape*.—Bi-parted.
*Ovary color*.—Not observed to date.
*Stamens*.—4.
*Found on only disc florets*.—Yes.
*Color of filaments*.—RHS 1C but greener.
*Length filaments*.—0.2-0.3 cm.
*Anther color*.—RHS 9A.
*Anther length*.—0.1 cm.
*Anther shape*.—Oblong.
*Color of pollen*.—Not observed to date.
*Pollen amount*.—Not observed to date.
*Fertility/seed set*.—Has not been observed to date on this hybrid.

Disease/pest resistance: Disease/pest resistance has not been observed to date on this hybrid.

What is claimed is:

1. A new and distinct variety of *Chrysanthemum* plant named 'CIDZ0004' substantially as illustrated and described herein.

* * * * *

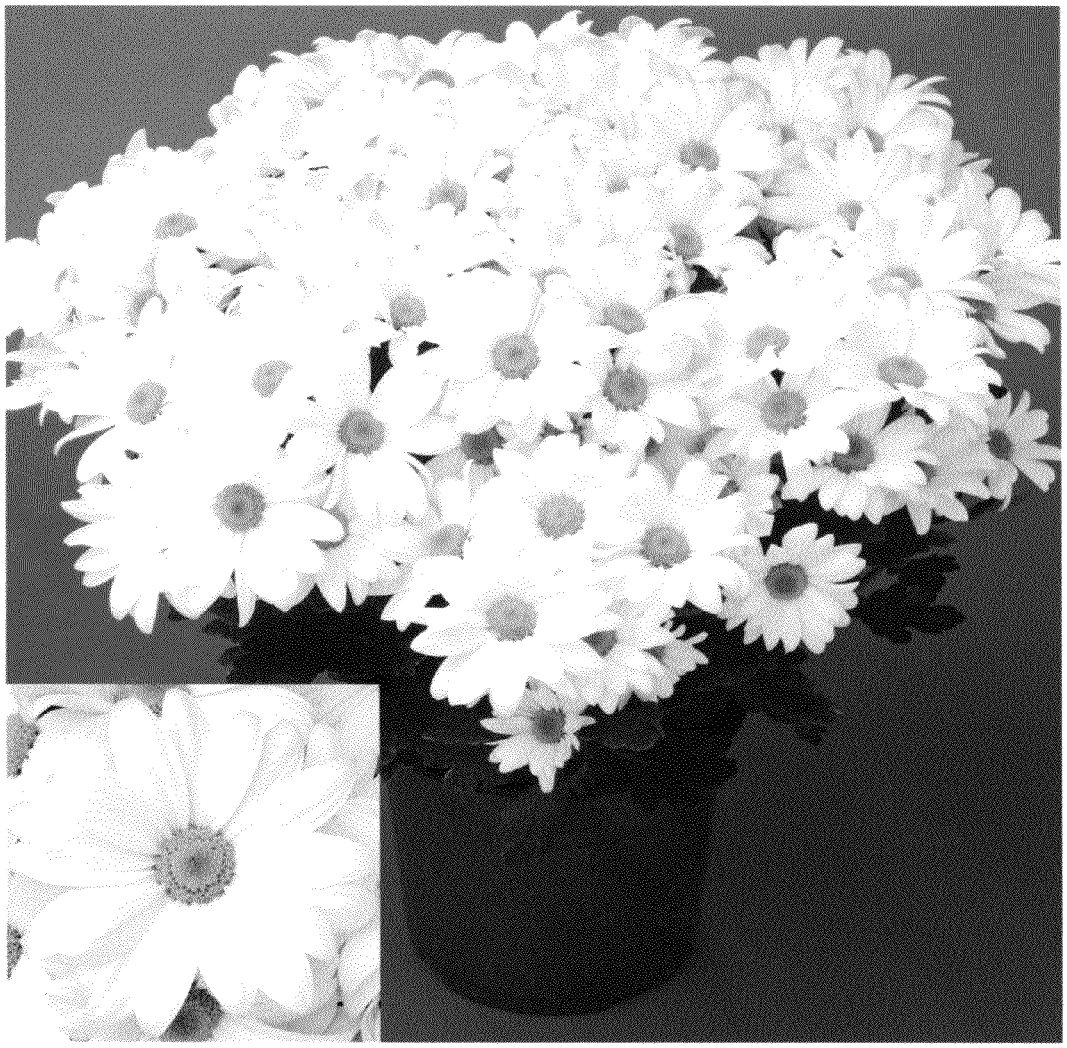

UNITED STATES PATENT AND TRADEMARK OFFICE

CERTIFICATE OF CORRECTION

PATENT NO. : PP22,957 P2
APPLICATION NO. : 13/136485
DATED : August 14, 2012
INVENTOR(S) : Bergman It is certified that error appears in the above-identified patent and that said Letters Patent is hereby corrected as shown below:

At column 3, line 62, insert --solitary-- before "daisy-type"

Signed and Sealed this
Twenty-fifth Day of September, 2012

David J. Kappos

David J. Kappos
*Director of the United States Patent and Trademark Office*